United States Patent [19]

Kruper, Jr. et al.

[11] Patent Number: 4,994,560

[45] Date of Patent: Feb. 19, 1991

[54] FUNCTIONALIZED POLYAMINE CHELANTS AND RADIOACTIVE RHODIUM COMPLEXES THEREOF FOR CONJUGATION TO ANTIBODIES

[75] Inventors: William J. Kruper, Jr., Sanford; Douglas K. Pollock, Midland; William A. Fordyce, Midland; Michael J. Fazio, Midland; Muthiah N. Inbasekaran, Midland, all of Mich.

[73] Assignee: The Dow Chemical Company, Midland, Mich.

[21] Appl. No.: 65,739

[22] Filed: Jun. 24, 1987

[51] Int. Cl.$^5$ .............................................. C07F 15/00
[52] U.S. Cl. ........................................ 534/10; 424/1.1
[58] Field of Search .......... 424/11 APS; 534/10 APS

[56] References Cited

U.S. PATENT DOCUMENTS 4,622,420  11/1986  Mears et al.
4,678,667  7/1987   Meares et al. .................... 424/9 X

OTHER PUBLICATIONS

Journal of Molecular Catalysis, 32 149–158, (1985), E. R. Savinova et al.,; "Catalysts for Dihydrogen Evolution from Water Based on Rhodium Complexes with Polyamines", part I. Structure of Phodium (III)-Polyamine Complexes.
Journal of Molecular Catalysis, 32 159–175, (1985), E. R. Savinova et al.; "Catalysts for Dihydrogen Evolution from Water Based on Rhodium-Polyamine Complexes Part II: The Activity of Catalysts and Nature of Their Active Components".
I. Tabushi et al., *Tetrahedron Letters* 12, 1049–1052 (1977).
D. E. Troutner and E. O. Schlemper, "Bifunctional Chelates of Rh-105 and Au-199 as Potential Radiotherapeutic Agents", Dept. of Energy Performance Report DOE/DE-FG02 86ER60400, Sep. 30, 1986.
T. Lynde-Kernell "Synthesis and Structural Studies of Rhodium(III) Complexes of Nitrogen Donor Ligands", Master Thesis, The Curators of the University of Missouri at Columbia, Dec. 1986.
Chen, Feng-Ming, "Metal Complexes of Tetradentate Nitrogen Ligands as Bifunctional Chelates for Radiolabling of Proteins", Ph.D. Thesis, The Curators of the University of Missouri at Columbia, 1985.

*Primary Examiner*—John S. Maples

[57] ABSTRACT

A group of functionalized polyamine chelants that form complexes with radioactive rhodium are disclosed. The rhodium complexes can be attached to an antibody or antibody fragment and used for therapeutic or diagnostic purposes.

16 Claims, No Drawings

FUNCTIONALIZED POLYAMINE CHELANTS AND RADIOACTIVE RHODIUM COMPLEXES THEREOF FOR CONJUGATION TO ANTIBODIES

BACKGROUND OF THE INVENTION

Functionalized chelants, or bifunctional coordinators, are known to be capable of being convalently attached to an antibody having specificity for cancer or tumor cell epitopes or antigens. Radionuclide complexes of such antibody/chelant conjugates are useful in diagnostic and/or therapeutic applications as a means of conveying the radionuclide to a cancer or tumor cell. See, for example, Meares et al., *Anal. Biochem.*, 142, pp. 68–78, (1984); and Krejcarek et al., *Biochem. and Biophys. Res. Comm.*, 77, pp. 581–585 (1977).

The methodology taught in the art to prepare such complexes involves treatment of an antibody/chelant conjugate with an excess of radionuclide to form a complex followed by purification of the complex. A major disadvantage of such methodology is that the radionuclide (a lanthanide or transition metal) must be kinetically labile in order to be rapidly sequestered by the antibody/chelant conjugate. This feature is disadvantageous in that the kinetic lability (or substitution lability) leads to problems associated with the serum stability of the complex. That is, the radionuclide readily dissociates from the complex in the presence of serum. Poor serum stability of such complexes leads to diminished therapeutic and/or diagnostic (imaging) effectiveness and poses a greater potential for general radiation damage to normal tissue (Cole et al., *J. Nucl. Med.*, 28, pp. 83–90 (1987)). More specifically, serum stability has been shown to be a problem with complexes containing hu 67Cu, $^{90}$Y, $^{57}$Co, and $^{111}$In (Brechbeil et al., *Inorg. Chem.*, 25, pp. 2772–2781 (1986)).

Another disadvantage associated with the use of labile radionuclides for antibody labelling is that substitutionally labile trace metals (which are not radioactive) are frequently incorporated into the chelate. Competition for such non-active trace metals diminishes the biological efficacy of the antibody/chelate complex since, inter alia, a lower quantity of radionuclide is delivered to the target site.

The majority of bifunctional coordinators or functionalized chelants which have been taught in the art to sequester radionuclides are carboxymethylated amine derivatives such as functionalized forms of ethylenediaminetetraacetic acid (EDTA) (U.S. Pat. No. 4,662,420) or diethylenetriaminepentaacetic acid (DTPA) (U.S. Pat. Nos. 4,479,930 and 4,454,106). In U.S. Pat. No. 4,622,420 it is generally taught that EDTA derivatives can also sequester ionic species of rhodium. However, rhodium, particularly rhodium (III), is know to be a substitution inert transition metal and it is further known that extreme conditions of temperature and duration are required to form its EDTA complex (Dwyer et al., *J. Amer. Chem. Soc.*, 83, pp. 4823–4826 (1960)). In addition, it has been reported that ethylenediaminedisuccinic acid will not form complexes with rhodium (III) at any pH below temperatures of 100° C (J. A. Neal and N. J. Rose, *Inorg. Chem.*, 12, 1225–1232 (1972)).

Tetraaza chelants (Troutner et al., *J. Nucl. Med.*, 21, pp. 443–448 (1980)) and alkylene amine oximes (U.S. Pat. No. 4,615,876) have been used to sequester $^{99m}$Tc, an isotope with nuclear properties suitable for diagnostic work only.

Rhodium-105 is both a gamma emitter (suitable for diagnostic work) and a short half-life beta emitter (suitable for therapeutic work). Because rhodium-105 can be used for both diagnostics and therapy, and because rhodium is substitution inert, it would be highly desirable to have functionalized chelants capable of forming complexes with radioactive rhodium that can be attached to an antibody. Tetraaza complexes of naturally occurring rhodium (III) are known in the literature for both linear (e.g., Bosnich et al., *J. Chem. Soc. Sec. A*, pp. 1331–1339 (1966)) and macrocyclic (E. J. Bounsall and S. R. Koprich, *Canadian Journal of Chemistry*, 48(10), pp. 1481–1491 (1970)) amines, however, functionalized polyaza chelates suitable for complexing radioactive rhodium and subsequent attachment to an antibody have been heretofore unknown.

SUMMARY OF THE INVENTION

The present invention is directed to bifunctional chelants that form complexes with rhodium. The bifunctional chelants preferably are used to complex radioactive rhodium, such as rhodium-105 ($^{105}$Rh) and rhodium-101$^m$ ($^{101m}$Rh). These bifunctional chelants would also be useful in complexing technetium and rhenium. The complexes so formed can be attached (covalently bonded) to an antibody or fragment thereof and use for therapeutic or diagnostic purposes. More specifically, the present invention is directed to a compound of the formula:

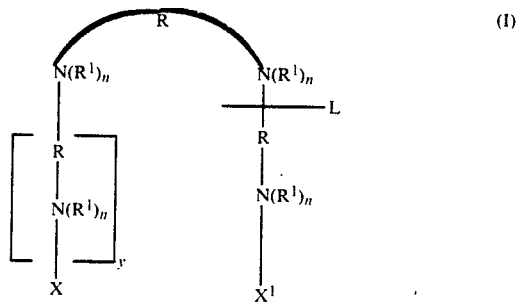

wherein each R independently represents a straight-chained or branched alkylene group of 2 to 10 carbon atoms inclusive (preferably of 2 or 3 carbon atoms), with the proviso that for any two adjacent nitrogens connected by an R group the R group must provide at least three single bonds between the nitrogens it connects;

each $R^1$ independently represents hydrogen or a straight-chained or branched alkylene group of 1 to 10 carbon atoms inclusive, preferably a hydrogen or methyl;

X and $X^1$ represent H, or X and $X^1$ taken together complete a bridging straight-chained or branched alkylene group of 2 to 10 carbon atoms inclusive or a bridging aralkylene wherein the alkylene is a straight-chained or branched alkylene group of 2 to 10 carbon atoms inclusive (preferably X and $X^1$ represent hydrogen or when taken together a benzyl or alkylene group of 2 or 3 carbon atoms) with the proviso that when X and $X^1$ are taken together the group it represents must provide at least three single bonds between the adjacent nitrogens it connects;

n is an integer of 0 of 1, provided that when the L group is bonded to the same nitrogen atom, n must be 0, otherwise n must be 1;

y is an integer of 1 through 3 inclusive, preferably the integer 1; and

L is a linker/spacer group convalently bonded to, and replaces one hydrogen atom of, any one of the nitrogen or carbon atoms, said linker/spacer group being represented by the formula

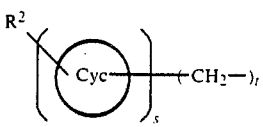

wherein s represents an integer of 0 or 1;

t represents an integer of 0 through 20 inclusive, preferably 0 through 6 inclusive;

$R^2$ represents an electrophilic or nucleophilic moiety which allows for covalent attachment to an antibody or fragment thereof, or a synthetic linker which can be attached to an antibody or fragment thereof; and Cyc represents a cyclic aliphatic moiety, aromatic moiety (preferably phenyl), aliphatic heterocyclic moiety, or aromatic heterocyclic moiety, each of said moieties optionally substituted with one or more groups which do not interfere with binding to an antibody or antibody fragment;

provided that the compound of formula I is not 3-(4-aminobutyl)-1,5,8,12-tetraazacyclotetradecane.

The present invention is also directed to rhodium complexes and to rhodium chelate/antibody conjugates formed with the aforementioned complexes; however, for such rhodium complexes and rhodium chelate/antibody conjugates there is no limitation with respect to 3-(4-aminobutyl)-1,5,8,12-tetraazacyclotetradecane. In addition, the present invention includes rhodium chelate/antibody compositions comprised of the rhodium chelate/antibody conjugates of the invention and a pharmaceutically acceptable carrier, typically in these compositions the pharmaceutically acceptable carrier is in liquid form. The invention also includes a method for the diagnosis or treatment of a disease state in a mammal by the administration of the rhodium chelate/antibody composition(s) and is particularly suited for the diagnosis and treatment of cancer.

Cyc will, for ease of reference, frequently be referred to herein simply as "Cyc". Of the Cyc moieties, phenyl, and substituted phenyl are preferred, with phenyl being the most preferred Cyc moiety.

As used herein, the following indicated terms having the following meanings: with respect to the definition of $R^2$; "electrophilic" moieties include, but are not limited to, isothiocyanate, bromoacetamide, maleimide, imidoester, thiophthalimide, N-hydroxysuccinimyl ester, pyridyl disulfide, and phenyl azide; suitable "nucleophilic" moieties include, but are not limited to, carboxyl, amino, acyl hydrozide, semicarbazide, and thiosemicarbazide; "synthetic linkers" include any synthetic organic or inorganic linkers which are capable of being covalently attached to an antibody or antibody fragment, preferred synthetic linkers are biodegradable synthetic linkers which are stable in the serum of a patient but which have a potential for enzymatic cleavage within an organ of clearance for the radioisotope, for example biodegradable peptides or peptide containing groups. Of the electrophilic moieties isothiocyanate is preferred and of the nucleophilic moieties amino, semicarbazide and thiosemicarbazide are preferred. It is desirable that the nature and/or position of $R^2$ be such that it does not appreciably interfere with the chelation reaction.

As used herein, the term "mammal" is used in its traditional sense and includes humans; "antibody" refers to any polyclonal, monoclonal, chimeric antibody or heteroantibody, preferably a monoclonal antibody; "antibody fragment" includes Fab fragments and F(ab')$_2$ fragments, and any portion of an antibody having specificity toward a desired epitope or epitopes. When using the term "rhodium chelate/antibody conjugate", "antibody" is meant to include whole antibodies and/or antibody fragments, including semisynthetic or genetically engineered variants thereof.

As used herein, "rhodium complex" refers to a complex of the compound of formula I wherein at least one rhodium atom is chelated or sequestered; "rhodium chelate/antibody conjugate" refers to a rhodium complex that is covalently attached to an antibody or antibody fragment; "naturally occurring" when used in conjunction with rhodium refers to the element in a form that is obtained when the element is purified from natural sources using standard procedures, that is, in a form that contains several isotopes, the vast bulk of which are non-radioactive; "radioactive" when use din conjunction with rhodium refers to one or more isotopes of the element that emit alpha, beta, and/or gamma particles, such as $^{105}$Rh; "rhodium" refers to either radioactive rhodium or naturally occurring rhodium or mixtures thereof; the terms "bifunctional coordinator" and "functionalized chelant" are used interchangeably and refer to compounds that have a chelant moiety capable of chelating rhodium and a linker/spacer moiety covalently bonded to the chelant moiety that is capable of serving as a means to covalently attach to an antibody or antibody fragment.

As used herein, "BA-cyclam" refers to the compound 3-(4-(aminophenyl)methyl-1,5,8,12-tetraazacyclotetradecane; "BA-2,3,2-tet" refers to the compound 6-(4-aminophenyl)methyl)-1,4,8,11-tetraazaundecane; "PA-2,3,2-tet" refers to the compound -6-(3-aminopropyl)-1,4,7,11-tetraazaundecane; and "BA-N-cyclen" refers to the compound 1,4,7,10-tetraaza-1-((4-aminophenyl)-methyl)cyclododecane. BA-cyclam, BA-2,3,2-tet, BA-N-cyclen and PA-2,3,2-tet are represented by the following formulae:

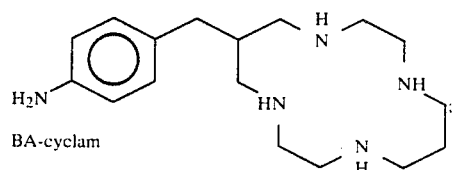

BA-cyclam

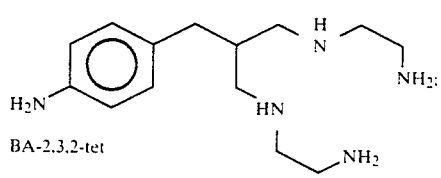

BA-2,3,2-tet

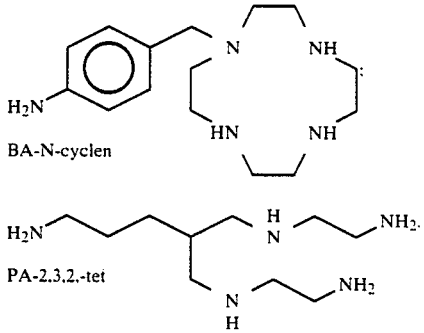

BA-N-cyclen

PA-2,3,2,-tet

Preferred compounds of formula I are BA-cyclam, BA-2,3,2-tet, PA-2,3,2-tet and BA-N-cyclen and the respective Rh(III) complexes thereof.

The preferred rhodium complexes of the present invention are salts that are represented by the formula $$[RhChP_1P_1]A \quad (II)$$

wherein Ch represents a compound of formula I; $P_1$ and $P_2$ represent monodentate ligands or if taken together, a bidentate ligand ($P_1P_2$), $P_1$ may be the same or different than $P_2$, provided, however, that: (a) $P_2$ are absent if y in formula I is 3. Examples of $P_1$ and $P_2$ are $F^-$, $Cl^{-1}$, $Br^-$, $I^-$, $CN^-$, $NCO^-$, $SCN^-$, $N_3^-$, $OH^-$, and $H_2O$, examples of $P_1P_2$ are $C_2O_4{}^{2-}$ and ethylenediamine; and A represents one or more anions of sufficient charge to render the entire complex neutral, members of A include $F^-$, $Cl^-$, $Br^-$, $I^-$, $CN^-$, $NCO^-$, $SCN^-$, $N_3^-$, $ClO_4^-$, $BF_4^-$, $BPh_4^-$, $NO_3^-$, and $PF_6^-$. In general, these rhodium complexes are prepared by refluxing, in aqueous solution, a simple rhodium starting material (e.g., rhodium halide hydrates) with the bifunctional coordinator. The pH can be titrated up to about $pH=7$ or controlled at approximately $pH=7$ with the use of a buffer. Generally, the ligands $P_1$ and $P_2$ will be the halide used in the rhodium starting material or $H_2O$. The counterion(s), A, will be the halide used in the rhodium starting material. Other ligands, $P_1$ and $P_2$, or counterions, A, may be substituted either by adding them to the initial reaction mixture or in a subsequent reflux step. The complexes are purified by column chromatography.

The functionalized polyamine described herein (that is, the compounds of formula I) can be used to chelate or sequester rhodium so as to form rhodium chelates (also referred to herein as "rhodium complexes"). The rhodium complexes because of the presence of the functionalizing moiety (represented by "L" in formula I) can be attached to functionalized supports, such as functionalized polymeric supports, or preferably covalently attached to antibodies or antibody fragments. The antibodies or antibody fragments which maybe used in the rhodium chelate/antibody conjugates described herein can be prepared by techniques well known in the art. Highly specific monoclonal antibodies can be produced by hybridization techniques well known in the art, see for example, Köhler and Milstein (*Nature*, 256, pp. 495–497 (1975); and *Eur. J. Immunol.*, 6, pp. 511–519 (1976)). Such antibodies normally have a highly specific reactivity. In the antibody targeted rhodium chelate/antibody conjugates antibodies directed against any desired antigen or hapten may be used. Preferably the antibodies which are used in the rhodium chelate/antibody conjugates are monoclonal antibodies, or fragments thereof having high specificity for a desired epitope(s). Antibodies used in the present invention may be directed against, for example, tumors, bacteria, fungi, viruses, parasites, mycoplasma, differentiation and other cell membrane antigens, pathogen surface antigens, toxins, enzymes, allergens, drugs and any biologically active molecules. For a more complete list of antigens see U.S. Pat. No. 4,193,983. The rhodium chelate/antibody conjugates are particularly preferred for the diagnosis and/or treatment of various cancers. The rhodium complexes and rhodium chelate/antibody conjugates described herein have excellent serum stability and/or excellent in vivo biolocalization. The rhodium chelate/antibody conjugates described herein can be administered in accordance with procedures well known in the art.

DETAILED DESCRIPTION OF THE INVENTION

The compounds of formula I can be prepared employing procedures known in the art. For example, compounds within the scope of formula I can be prepared employing synthesis methodologies such as Synthesis Schemes A-D which follow:

Synthesis Scheme A

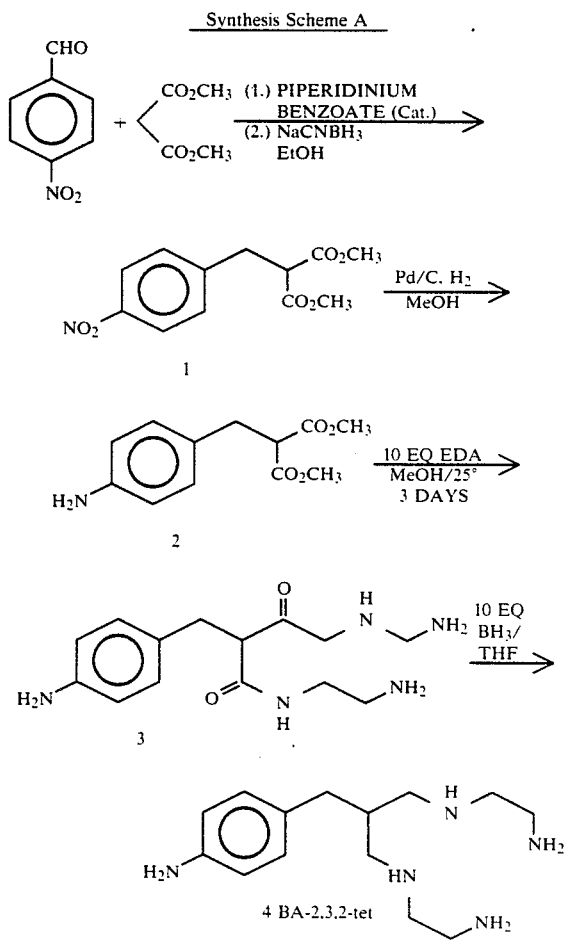

Synthesis Scheme B

-continued

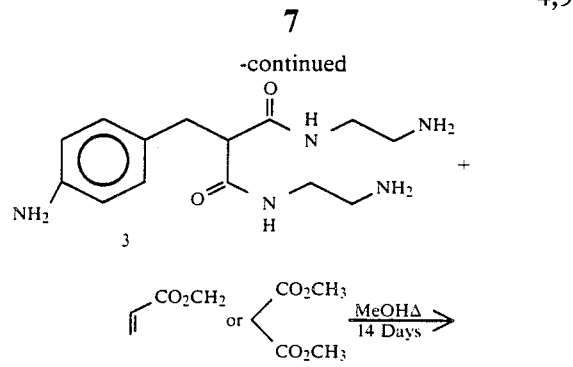

3

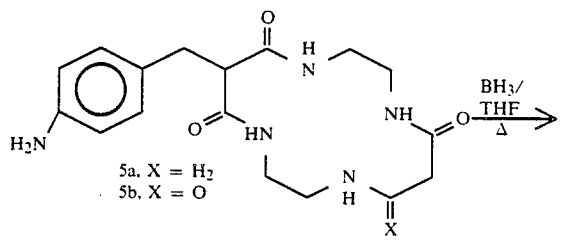

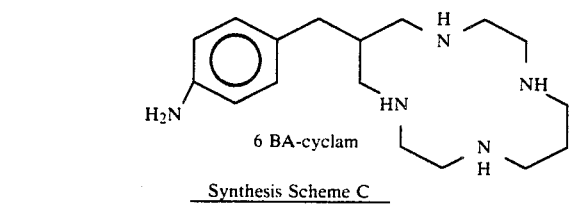

5a, X = H₂
5b, X = O

6 BA-cyclam

Synthesis Scheme C

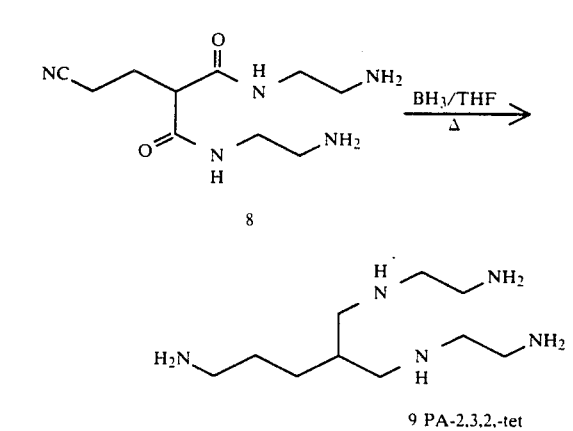

7

8

9 PA-2,3,2,-tet

Synthesis Scheme D

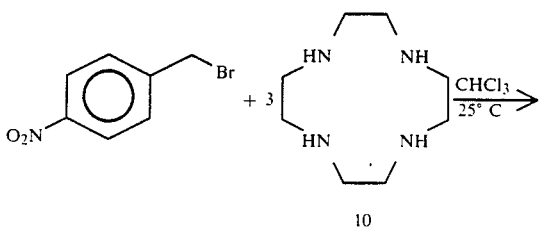

10

-continued
Synthesis Scheme D

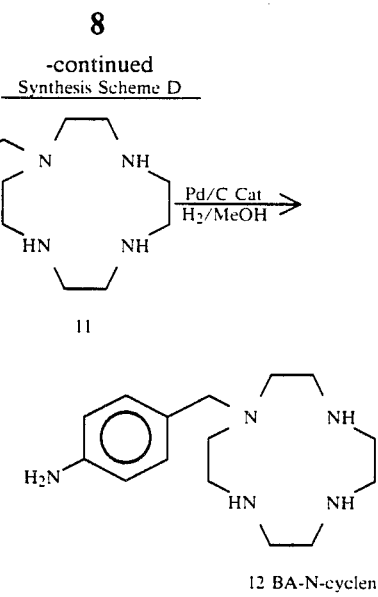

11

12 BA-N-cyclen

BACKGROUND OF THE INVENTION

The four bifunctional ligand systems which have been synthesized in the course of this work (i.e., BA-2,3,2-tet, PA-2,3,2-tet, BA-cyclam and BA-N-cyclen) are specific examples of the generic bifunctional structure depicted by formula I. There are two major types of polyaza (number of nitrogen chelating atoms=4-6) compounds which are representative of the generic structure: (1) Linear polyaza compounds with a spacer/linker group covalently attached to this moiety (e.g., BA-2,3,2-tet or PA-2,3,2-tet); and (2) Macrocyclic polyaza compounds with a spacer/linker covalently attached (e.g., BA-cyclam or BA-N-cyclen).

Both major types can be subdivided further in terms of how the spacer/linker group can be covalently attached to the chelating polyaza moiety. Conceptually, attachment can be made through annelation either at a carbon atom (e.g., BA-cyclam, BA-2,3,2-tet, PA-2,3,2-tet) or a nitrogen atom (e.g., BA-N-cyclen).

Synthesis Scheme D depicts a methodology which is amenable to the synthesis of any nitrogen annelated linker/spacer group. The generality of this approach has been recently documented in the literature (E. Kimura et al., *J. Chem. Soc., Chem. Comm.*, pp. 1158–1159 (1986)) and provides a method for monoalkylating any polyazamacrocycle with a suitable electrophile (i.e., linker/spacer) which could contain a latent functionality enabling antibody conjugation. A variety of polyaza macrocycles are available commercially or have been made using the tosylate displacement/macrocyclization techniques noted in the literature (T. J. Atkins et al., *Org. Synth.*, Vol. 58; Ed. W. A. Sheppard, John Wiley and Sons, New York, 1978 pp. 86–97). Clearly, the N-alkylation approach offers the greatest versatility through a convergent synthetic route.

Linear or macrocyclic ligands which are connected to the linker/spacer through a carbon atoms attachment may be arrived at through primarily three established methodologies. Macrocylic amines containing four and five nitrogen atoms have been made from condensation of the appropriately substituted malonate ester with linear tetraamines or pentaamines (Tabushi et al., *Tetrahedron Letters*, 12, pp. 1049–1052 (1977) and Machida et al., *Inorg. Chem.*, 25, pp. 3461–3466 (1986)). The aforementioned article of Tabushi et al. describes the compound 3-(4-aminobutyl)-1,5,8,12-tetraazacyclotetradecane. A second approach to carbon annelated macrocycles such as BA-cyclam involves malonate ester displacement with a large excess of diamine (Schemes A & C) and ring closure with acrylate or malonate (SCheme B). The versatility of this approach has been noted in the literature (E. Kimura et al., *Inorg. Chem.*, 23, pp. 4181-4188 (1984)) and can also be used to make linear polyaza compounds of variable ligand/metal bite size.

Both of these approaches involve nucleophilic attack of the amine or aza compound on an ester or acyl functionality. Thus a reduction step is necessary to convert the amide to the polyamine.

A third potential method for synthesizing macrocycles containing a carbon annelated linker/spacer group would involve a macrocyclization via $S_N2$ or simple aliphatic displacement chemistry. To date, this strategy has only been applied toward the synthesis of mono-N-substituted tetraazamacrocycles (N. Alcock et al., *J. Chem. Soc. Dalton Trans.*, pp. 2371-2376 (1984)). However, this technique could be applied to the synthesis of carbon annelated systems as well:

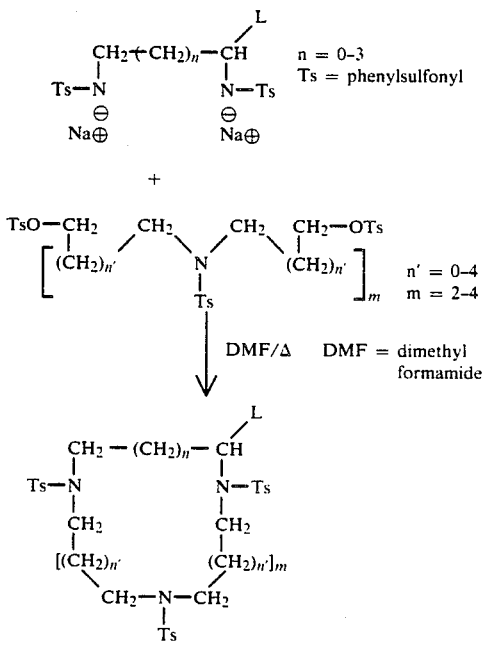

The tosylate groups can be easily removed by a variety of procedures known in the art. It should be appreciated that most any specific bifunctional coordinator generically encompassed by formula I could be made using one of the general approaches outlined here. Surprisingly, there is no example of an antibody conjugatable tetramine rhodium complex which is documented in the literature.

The following examples are given to illustrate the invention, but should not be construed to limit the invention.

GENERAL EXPERIMENTAL

Mass spectra were obtained on either a Finnigan TSQ mass spectrometer ($Q_1$ MS mode) or a VG ZAB-MS high resolution mass spectrometer (fast atom bombardment with Xenon). $^1H$ and $^{13}C$ NMR were obtained using a Varian VXR-300 spectrometer. Infrared (IR) spectra were recorded on a Nicolet S5X FT/IR instrument.

All solvents employed were Fisher HPLC grade materials which were used without further purification. All preparative chromatography of organic compounds (Schemes A-D) was performed using the flash chromatography technique noted in the literature[1] (Merck Grade 60, 230-400 mesh silica gel, 60Å-Aldrich Chemical Company) using the following solvent systems: (1) Solvent system 1-CHCl$_3$/MeOH/NH$_4$OH-2/2/1; (2) Solvent system 2-CHCl$_3$/MeOH/NH$_4$OH-12/4/1; (3) Solvent system 3-CHCl$_3$/MeOH/NH$_4$OH-16/4/1 v/v. R$_f$ values are reported using these solvent systems and commercially available Analtech silica plates (250 micron, Analtech Inc.).

[1]W. C. Still, M. Kahn and A. Mitra, *J. Org. Chem.*, 43, pp. 2923-2925 (1978)

EXAMPLE 1

2-Carbomethoxy-3-(4-nitrophenyl)propanoic acid methyl ester (p-nitrobenzyl malonate dimethyl ester), 1

2-Carbomethoxy-3-(4-nitrophenyl)propanoic acid dimethyl ester was made from the Knovenagle condensation of dimethylmalonate and p-nitrobenzaldehyde according to the method of Baker and Eccles[2]. Melting point observed (mp$_{pbs}$) = 133°-134° C. Melting point reported in the literature (mp$_{lit}$) = 136°-137° C[2].2-Carbomethoxy-3(4-nitrophenyl)propanoic acid methyl ester (23.0 grams (g), 86.7 millimoles (mmole)) was dissolved in 175 milliliters (ml) of methanol (MeOH) under nitrogen and sodium cyanoborohydride[3](6.0 g, 95.5 mmole) was cautiously added to the stirred solution with cooling. The pH was adjusted to 4.0 with concentrated hydrochloric acid and the solution was stirred at 25° C overnight. During the first eight hours the pH was readjusted from 6 to 4 on several occasions. The yellow methanol solution was poured into 700 ml of water and extracted with 3×200 ml portions of methylene chloride. The combined organic fractions were washed with 400 ml of saturated sodium bicarbonate and 400 ml of water, dried over magnesium sulfate and evaporated to a pale yellow oil on a rotary evaporator. The oil crystallized (mp$_{obs}$=82-83° C; mp$_{lit}$=82-.5-83.5° C) upon standing and gave 2-carbomethoxy-3-(4-nitrphenyl)propanoic acid methyl ester (p-nitrobenzyl malonate dimethyl ester) in 93 percent yield (21.3 g, 81 mmole).

[2]J. W. Baker and A. Eccles, *J. Chem. Soc.* (1927), pp. 2125-2133.
[3]R. O. Hutchins, D. Rotstein, N. Natale, J. Fanelli and D. Dimmel, *J. Org. Chem.*, 41, p. 3328 (1976).

EXAMPLE 2

3-(4Aminophenyl)-2-carbomethoxypropanoic acid methyl ester (p-aminobenzylmalonate dimethyl ester), 2

The compound 2-carbomethoxy-3-(4-nitrophenyl)-propanoic acid methyl ester (p-nitrobenzyl malonate dimethyl ester) (2.00 g, 7.55 mmole) was dissolved in 70 ml of ethyl acetate containing 5 percent palladiunm on carbon (1.0 g-Aldrich Chemical Company) catalyst and was hydrogenated in a Parr shaker employing 50 psig of hydrogen at 22° C. Hydrogen uptake was rapid (15 minutes) and the mixture was maintained under hydrogen pressure for another three hours. The pressure vessel was vented and flushed with nitrogen (N$_2$). The suspension was filtered through a pad of celite and the solvent was removed in vacuo using a rotary evaporator to provide 3-(4-aminophenyl)-2-carbomethoxypropanoic acid methyl ester (p-aminobenzylmalonate dimethyl ester) (1.76 g, 7.41 mmole) as a light yellow oil in 98 percent yield. The structure was confirmed by $^1$H nuclear magnetic resonance (PNMR) and $^{13}$C nuclear magnetic resonance (CMR) as well as mass spectroscopy (MS) spectral analysis.

EXAMPLE 3

6-(4-Aminophenyl)methyl)-1,4,8,11-tetraaza-5,7-dioxoundecane, 3

The compound 3-(4-aminophenyl)-2-carbomethoxypropanoic acid methyl ester (p-aminobenzylmalonate dimethyl ester) (30.0 g, 0.126 mole) was added dropwise to a solution of ethylene diamine (75 g, 125 mole) in 150 ml of methanol under a nitrogen atmosphere with vigorous stirring (25° C). The solution was allowed to stir for 4 days until reaction was judged complete by thin layer chromatography (TLC). At this point the solvent and excess amine were removed in vacuo and the tan residue was dried overnight (70° C /0.1 mm) affording 36.3 g of the desired compound 6-(4(aminophenyl)methyl)-1,4,8,11-tetraaza-5,7-dioxoundecane as a tan solid in 98 percent yield. An analytical sample was prepared by recrystallization from chloroform/hexane, mp=157°-159° C, as a white crystalline powder. Structure was confirmed by PMR, CMR, and MS.

| Analysis | C | H | N |
|---|---|---|---|
| Calculated for $C_{14}H_{23}O_2N_5$: | 57.3 | 7.90 | 23.87 |
| Found: | 57.16 | 7.48 | 23.65 |

EXAMPLE 4

6-(4-(Aminophenyl)methyl)-1,4,8,11-tetraazaundecane, (BA-2,3,2-Tet), 4

The compound (6-(4-(aminophenyl)methyl)-1,4,8,11-tetraaza-5,7-dioxoundecane (7.0 g, 23.9 mmole) was placed in a 3-necked, 250 ml round bottomed flask equipped with a stirrer and reflux condenser under a nitrogen atmosphere. Borane/tetrahydrofuran (THF) complex (150 ml, 150 mmole) (Aldrich Chem. Co.) was slowly added via a cannula under positive nitrogen pressure to the solid with stirring. A brief exotherm was noted and after it subsided, the stirred solution was taken to reflux for 48 hours (hrs). The clear solution was stripped of solvent in vacuo leaving a glassy, semi-solid material. Methanol (100 ml) was cautiously added and hydrogen evolution was noted. The resulting solution was taken to dryness in vacuo. At this point, 100 ml of methanol was added and the solution saturated with anhydrous hydrogen chloride. The solution was brought to reflux under nitrogen for 1 hour and stripped of solvent using a rotary evaporator. This cycle was repeated and the resulting crude hydrochloride salt of the desired compound was dissolved in 15 ml of water. This fraction was extracted with 2×20 ml portions of chloroform (CHCl$_3$) and the aqueous phase was then made basic (pH>12) by the addition of 50 percent aqueous sodium hydroxide with cooling under argon. The basic solution was extracted with 6×75 ml portions of chloroform. These fractions were combined (no drying) and the chloroform was removed in vacuo to afford 5.8 g of crude amine as a yellow oil (91 percent). The crude material was purified by flash chromatography using a 16:4:1 solvent of chloroform:methanol: concentrated ammonium hydroxide and silica gel (Aldrich Chemical Co./Merck grade 60 230-400 mesh), (R$_f$=0.33 solvent 1). The structure of purified product was confirmed by PMR, CMR, and MS.

| Analysis | C | H | N |
|---|---|---|---|
| Calculated for $C_{14}H_{27}N_5$.5HCl: | 37.56 | 7.20 | 15.64 |
| Found: | 37.5 | 6.42 | 15.83 |

EXAMPLE 5

3-(4-(Aminophenyl)methyl)-1,5,8,12-tetraaza-2,4,9-trioxocyclotetradecane, (BA-Cyclamtriamide), 5a The compound 6-(4-(aminophenyl)methyl)-1,4,8,14-tetraaza-5,7-dioxotetradecane (15.0 g, 51.1 mmole) and methylacrylate (4.29 g, 51.1 mole) were dissolved in 800 ml of methanol (MeOH) under nitrogen with stirring. After 40 hours at room temperature (25° C), the solution was brought to reflux for 13 days. Upon cooling a white precipitate formed. The solvent was removed using a rotary evaporator and the resulting waxy solid was chromatographed using a 350:35:5 solution of chloroform:methanol:concentrated ammonium hydroxide and the flash chromatography technique. The desired compound 3-(4-(aminophenyl)methyl)-1,5,8,12-tetraaza-2,4,9-trioxocyclotetradecane was obtained (7.5 g, 21.6 mmole) in 42 percent yield as a white solid (R$_f$=0.62/solvent; mp=250-252C.

| Analysis | C | H | N |
|---|---|---|---|
| Calculated for $C_{17}H_{25}N_5O_3$: | 58.77 | 7.25 | 20.16 |
| Found: | 58.03 | 7.26 | 19.81 |

EXAMPLE 6

3-(4-(Aminophenyl)methyl)-1,5,8,12-tetraazacyclotetradecane, (BA-Cyclam), 6

The compound 3-(4-(aminophenyl)methyl)-1,5,8,12-tetraaaza-2,4,9-trioxocyclotetradecan (2.5 g, 7.20 mmole) was refluxed in 200 ml of 1 M borane/THF complex under nitrogen for 50 hours. Workup in a fashion similar to Example 4 yielded the crude hydrochloride salt. The salt was dissolved in 20 ml of water and extracted with 2×100 ml portions of chloroform. The aqueous layer was cooled to 0°-5° C under argon and was extracted with 3×100 ml portions of chloroform which were combined, filtered through a glass wool plug and evaporated to dryness (high vacuum) to yield 2.1 g (7.0 mmole) of the desired product 3-(4-(aminophenyl)methyl)-1,5,8,12-tetraazacyclotetradecane as a white solid in 97 percent yield (mp=156°-158° C). Structure was confirmed by PMR and CMR.

| Analysis | C | H | N |
|---|---|---|---|
| Calculated for $C_{17}H_{31}N_5.H_2O$ | 63.12 | 10.28 | 21.65 |
| Found: | 63.65 | 9.92 | 21.60 |

EXAMPLE 7

3-(4-(Aminophenyl)methyl)-1,5,8,12-tetraaza-2,4,9,11-tetraoxocyclotetradecane, (BA-Cyclamtetraamide), 5b The compound 6-(4-(aminophenyl)methyl)-1,4,8,11-tetraaza-5,7-dioxoundecane (7.03 g, 24 mmole) and dimethylmalonate (3.17 g, 24 mmole) in 50 ml of methanol were heated under gentle reflux with stirring under N₂ for 4 days. The mixture was cooled and the colorless precipitate which was obtained was filtered. This material was then chromatographed on silica gel by flash chromatography elution with a 85:10:2 v/v/v mixture of chloroform:methanol:concentrated ammonium hydroxide. The crude material was recrystallized from methanol and gave 3-(4-aminophenyl)methyl)-1,5,8,12-tetraaza-2,4,9,11-tetraoxocyclotetradecane as colorless crystals (2.01 g, 24 percent) mp 288°-290° C (dec) which was characterized by IR, PMR and CMR techniques.

EXAMPLE 8

BA-cyclam, 6

The compound 3-(4-(aminophenyl)methyl)-1,5,8,12-tetraaza-2,4,9,11-tetraococyclotetradecane prepared in Example 7 was reduced with diborane (reflux, 18 hours) in tetrahydrofuran (THF) to give 4-aminobenzyl cyclam in 55.3 percent yield. The material had properties substantially as described in Example 6.

EXAMPLE 9

1,4,8,11-Tetraaza-6-(2-cyanoethyl)-5,7-dioxoundecane, 8

Diethyl 2-(2-cyanoethyl)malonate 7 (5.0 g, 23.5 mmole-Aldrich Chemical Company) was added dropwise over a one hour period to a stirred portion of freshly distilled ethylene diamine (15 g, 0.25 mole) which was maintained under nitrogen at 0° C. The stirred solution was allowed to warm to room temperature (25° C) and stirring was continued over a four day period. At this point, the excess ethylene diamine was removed in vacuo with care to avoid heating over 40° C. The crude clear oil which resulted was subjected to flash chromatography using Solvent System 3 as the eluent to give 2.3 g (8.81 mmole) of 1,4,8,11-tetraaza-6-(2-cyanoethyl)-5,7-dioxoundecane as a clear viscous oil in 37 percent yield (R$_f$=0.39/Solvent System 3): $^1$H NMR (CDCl₃) δ 7.59 (t, 2H, J=3.1 H₃, amide H), 3.29 (m, 5H, methine H and α amido CH₂), 2.82 (dt, 4H, J₁=4.0 H₃, J₂−0.8 H₃), β amido CH₂) 2.48 (t, 2H, J₃=7.1, α nitrile CH₂), 2.21 (q, 2H, J₃=7.1 H₃, β nitrile CH₂),1.39 (S, 4H, amino NH); $^{13}$C NMR (CDCl₃)δ 169.6 (amide carbonyl), 118.9 (nitrile), 52.9, 42,3, 412., 27.1, 15.4.

EXAMPLE 10

6-(3-Aminopropyl)-1,4,8,11-tetraazaundecane, PA-2,3,2-Tet, 9

The compound 1,4,8,11-tetraaza-6-(2-cyanoethyl)-5,7-dioxoundecane (1.6 g, 6.13 mmole) from Example 9 was refluxed under nitrogen in 1 M borane/THF (200 ml) solution for 40 hours. Methanol/hydrogen chloride reflux as noted in Example 4 and workup provided 1.5 g of the crude hydrogen chloride salt of 6-(3-aminopropyl)-1,4,8,11-tetraazaundecane. This material was dissolved in 1.5 ml of water and 50 percent sodium hydroxide was added. (pH–13) with gasliberation noted. The free base was extracted with 3×7 ml portions of acetonitrile using a Mixor (Liddex Corporation, Ltd., Haifa Israel) extractor. The combined organic phase was reduced using a rotary evaporator and the clear oil was applied to a short pad of flash silica gel as a chloroform solution. The product 6-(3-aminopropyl)-1,4,8,11-tetraazaundecane was isolated as a clear oil using Solvent System 1 as an eluent after solvent removal (R$_f$=0.04/Solvent System 1). Free base was dissolved in 5 ml of methanol which was subsequently saturated with anhydrous hydrogen chloride. Evaporation to dryness afforded 350 mg of 6-(3-aminopropyl)-1,4,8,11-tetraazaundecane as the hydrochloride salt (15 percent yield): $^1$H NMR (D₂O, pH=1.5) δ 3.47 (m, 8H), 3.34 (m, 4H), 3.06 (t, 2H, J=3.8 H₃, α methylene to distal amine), 2.41 (P, 1H, J=3.8 H₃, methine), 1.78 (m, 2H), 1.67 (m, 2H); $^{13}$C NMR (D₂O, pH=1.5) δ 51.5, 47.7, 37.9, 36.1, 28.1, 25.7.

EXAMPLE 11

1,4,7,10-Tetraaza-1-((4-nitrophenyl)methyl)cyclododecane, 11

1,4,7,10-Tetraazacyclododecane, 10, (270 mg, 1.67 mmole) prepared by the method of Richman and Adkins④was dissolved in 5 ml of chloroform. p-Nitrobenzyl bromide (113 mg, 0.52 mmole-Aldrich Chemical Company) was added to this solution and stirring was commenced for 14 hours. Thin layer chromatography revealed a strongly ninhydrin positive spot (R$_f$=0.58/Solvent System 3) different from the starting materials. The solution was applied to 17×1 centimeter (cm) flash silica gel column and eluted with Solvent System 3. Fractions devoid of starting materials were combined and evaporated affording 109 mg of analytically pure, pale yellow crystals of 1,4,7,10-tetraaza-1-((4-nitrophenyl)methyl)cyclododecane in 68 percent yield, mp=128°-129° C. Structure was confirmed by NMR.

| Analysis | C | H | N |
|---|---|---|---|
| Calculated for C₁₅H₂₅N₅O₂: | 58.61 | 8.20 | 22.78 |
| Found: | 58.4 | 8.30 | 22.80 |

④. E. Richman and T. J. Adkins. *J. Amer. Chem. Soc.*. 96. 2268-2269 (1974).

EXAMPLE 12

1,4,7,10-Tetraaza-1-((4-aminophenyl)methyl)cyclododecane, (BA-N-Cyclen), 12

The compound 1,4,7,10-tetraaza-1-((4-nitrophenyl)methyl)cyclododecane (170 mg, 0.55 mmole) was dissolved in 5 ml of methanol and 100 mg of 10% palladium on carbon (Lancaster Synthesis Ltd.) was added to this solution with stirring. A steady stream of hydrogen gas was bubbled through the stirred mixture. Within thirty minutes, thin layer chromatography analysis suggested total conversion of 1,4,7,10-tetraaza-1-((4-nitrophenyl)methyl)cyclododecane to 1,4,7,10-tetraaza-1-((4-aminophenyl)methyl)cyclododecane, (R$_f$=0.28/Solvent System 3). The solution was purged with nitrogen and filtered through a short plug of celite. Evaporation of solvent and flash chromatography (Solvent System 3) provided 103 mg of 1,4,7,10tetraaza-1-((4-aminophenyl)methyl)cyclododecane in 67 percent yield. The structure was confirmed by $^1$H and $^{13}$C NMR analysis. The free base was converted to the tetrahydrochloride salt (mp=255°-260° C (dec))—pale yellow powder.

EXAMPLE 13

$^{105}$Rh was obtained using a system in which five flasks were interconnected via ground glass fittings in the following order: a first flask (a catch flask employed as a gas trap), a second flask (the reaction vessel), a third flask (trap #1), a fourth flask (trap #2), and a fifth flask (trap #3).

Into the reaction vessel was placed 10 ml of 2 M NaOH. To trap #1 was added 150 ml of CCl₄, to trap #2 was added 150 ml of 2 M NaOH and to trap #3 was added 150 ml of 2 M NaOH. A quantity of Ruthenium metal (5.18 mg) which had been irradiated for 30 minutes in the 1st row p-tube at MURR (University of Missouri Research Reactor) on the previous day, was added to the reaction vessel. Stoppers were placed in the tops of the first four flasks. Cl₂ was bubbled through the apparatus for approximately 10 minutes, the solution in the reaction vessel turned bright yellow. A stream of air was then passed through the apparatus for 20 minutes and the reaction vessel was heated to reflux for approximately 5 minutes employing a heating mantle. During this process, the solution int eh reaction vessel became clear and the CCl₄ in trap #1 turned bright yellow. The solution was removed from the reaction vessel and filtered through a 0.2 mm filter. A quantity of the reaction vessel solution (1.0 ml) was taken and diluted to 10 ml in a scintillation vial for counting. A quantity of 10 ml of each of the solutions contained in traps #1, #2 and #3 were also taken for counting. The solution in the reaction vessel contained the $^{105}$Rh.

EXAMPLE 14

The following example illustrates the preparation of rhodium chelate complexes using methods similar to those reported by S. A. Johnson and F. Basolo, *Inorg. Chem.* (1962), 1, pp. 925–932.

A. Materials and Techniques

Rhodium trichloride hydrate and lithium hydroxide (LiOH) (99.3 percent, anhydrous, −4+14 mesh) were obtained from Johnson Matthey and Alfa respectively. The chelants BA-2,3,2-tet·5HCl and BA-cyclam·5HCl were prepared as described in Examples 4 and 6.

Pharmacia Sephadex-SP ™ C-25 cation-exchange resin was purchased from Aldrich. Glass columns for chromatography were approximately 2.5×70 cm and fitted with a 29/42 ground glass joint at the top and a course glass frit and teflon stopcock at the bottom. The cation-exchange resin was prepared by adding 40 g of dry gel to 300 ml of 0.3 N aqueous HCl with gentle stirring to form a slurry. The slurry was then transferred to a large graduated cylinder and allowed to swell over a 1.5 hr period. At several intervals during this period a portion of the 0.3 N HCl was decanted off (in an effort to remove fines), additional 0.3 N HCl was added, and the slurry was gently mixed. The column was poured by attaching a 1 liter Kugelrohr flask to the top of the column and transferring the slurry all at once. The gel was converted to the H⁺ form and packed by running 2-3 liters of 0.3 N HCl through the column.

Samples (0.1 to 1.0 g) were chromatographed by dissolution in 5–10 ml distilled water and application of the solution directly to the top of the column. The solution was washed into the gel with several small portions of 0.3 N HCl and eluted down the column with the same solvent. The solvent flow rate through the column was maintained with a Gilson Miniplus 2 peristaltic pump (3-4 per minute (min⁻¹)) and eluted sample peaks were detected at 254 nanometers (nm) with an Isco model UA-5 absorbance monitor with a model 1132 multiplexer-expander and type 6 optical unit. Neutral, negatively charged, and mono-positively charged species eluted off the column quickly (0.5–1.5 hrs), di-positively charged species eluted off after 5–8 hrs, and more highly positively charged species remained at the top of the column.

B. [Rh(BA-2,3,2-tet)Cl₂]Cl·HCl

With minor modifications, the method of Martins and Seridan (Martins, E.; Sheridan, P. S., *Inorg. Chem.* (1978), 17, pp. 2822–2826) for the preparation of dichloro (β, β', β''-triaminotriethylamine)rhodium(III) chloride was used. RhCl₃·3H₂O (0.308 g, 263.309 g mol⁻¹, 1.17 mmole) was added to a solution of BA-2,3,2-tet·5HCl (0.524 g, 447.71 g mol⁻¹, 1.17 mmole) in 30 ml of 0.1 N LiPH. The red solution was refluxed for 5 minutes and then slowly titrated up to pH=6 over a 45 minutes period using 0.1 N LiPH (a total of 64.1 ml was used or 5.5 equivalents). The pH was monitored using colorpHast ™ indicator strips (obtained from Macalaster Bicknell Co.). After a total of approximately 1 hr of reflux the yellow-brown mixture was cooled, filtered, and the solvent removed on a rotary evaporator. The solid was dissolved in 10 ml of distilled water, filtered through a Celite ™ pad on a fine porosity glass fritted filter and Gleman Acrodisc# CR disposable syringe tip filter (obtained from Fisher Scientific), and applied to the top of a Spehadex-SP ™ C-25 column (see above). The di-positively charged species were eluted off the column as a single band with 0.3 N HCl and a fraction was collected. The solvent was removed on a rotary evaporator and the yellow solid was dried at 30° C in a vacuum oven yielding 0.205 mg of product (34.3 percent). The material was characterized by ¹H and ¹³C NMR and fast atom bombardment mass spectroscopy. NMR spectroscopy indicated that the product existed in three isomeric forms.

| Analysis | C | H | N |
| --- | --- | --- | --- |
| Calculated C₁₄H₂₇N₅Cl₃Rh·HCl·2H₂O: | 30.73 | 5.90 | 12.80 |
| Found: | 30.5 | 5.4 | 12.5 |

C. [Rh(BA-cyclam)Cl₂]Cl·HCl

The method was the same as that described above except that 0.50 g RhCl₃·3H₂O (1.90 mmole), 0.93 g BA-cyclam·5HCl (1.91 mmole), and 102.5 ml 0.1 N LiPH (10.3 mmole, 5.39 equivalents) were used yielding 0.385 g of product (36.8 percent). The product was characterized as described above. NMR spectroscopy indicated the presence of multiple isomers.

| Analysis | C | H | N |
| --- | --- | --- | --- |
| Calculated C₁₇H₃₁N₅Cl₃Rh·HCl·2H₂O: | 34.77 | 6.18 | 11.93 |
| Found: | 34.6 | 5.6 | 11.6 |

EXAMPLE 15

Preparation of [$^{105}$Rh(BA-2,3,2-tet)Cl₂]$^{30}$ $^{105}$Rhodium chloride (approximately 5 mCi/ml in 0.1 N HCl) was obtained from the University of Missouri research reactor. Three milliliters of this stock solution was neutralized by the addition of 0.4 ml of 1.0 M NaHCO₃. BA-2,3,2-tet (0.2 ml of a 10 mg/ml solution) was added with mixing. This solution was heated to 90° C in a water bath for 1 hour. Purification of the $^{105}$Rh complexes from any unbound metal and chelant was achieved by passing the solution through a Hamilton PRP-1 Chrompak Unit. The $^{105}$Rh complexes were eluted with a 30 percent acetonitrile/water wash. Analysis of this material indicated the presence of equal parts of the [$^{105}$Rh(BA-2,3,2-tet)Cl$_2$]$^+$ and [$^{104}$Rh(Ba-2,3,2-tet)(Cl)(H$_2$O)]$^{2+}$ complexes. The aquochloro complex was converted to the dichloro complex by making the solution 0.5 N in HCl and heating to 90° C in a water bath for an additional 30 minutes. The ]$^{105}$Rh(BA-2,3,2-tet)Cl$_2$]$^+$ complex was isolated and concentrated with the Hamilton PRP-1 Chrompak. The complex was characterized by comparison to known standard material using cation exchange chromatography and thin layer chromatography. Yields of greater than 85 percent with respect to the $^{105}$Rh were obtained.

EXAMPLE 16

Conjugation of [$^{105}$Rh(BA-2,3,2-tet)Cl$_2$]$^{30}$ to Antibody

The [$^{105}$Rh(BA-2,3,2-tet)Cl$_2$]$^+$ complex was conjugated to an antibody through the carbohydrate side chains following the basic procedure outlined by Murayama et al. (A. Murayama, K. Shimada and T. Yamamoto, Immunichemistry, 15, pp. 523–528, (1978)). The antibody used was CC-49, a murine monoclonal IgG, that binds to an epitope of TAG-72, a tumor associated antigen. One mg of the purified CC-49 IgG (10 mg/ml in 0.05 M sodium acetate pH 5.2) was treated with 1 mmole (0.010 ml of a 0.100 M solution) of NaIO$_4$ for 1 hour at room temperature in the dark. This activated antibody was separated and recovered from the excess NaIO$_4$ by centrifugal gel filtration. To the activated antibody, 0.100 ml of the [$^{105}$Rh(BA-2,3,2-tet)Cl$_2$]$^+$ complex (approximately 5 mCi/ml, 1×10$^{-4}$ M) and 0.010 ml of NaCNBH$_4$ (0.10 M) were added. Coupling was allowed to proceed 2 hours at room temperature. The $^{105}$Rh labeled antibody was isolated by repeating the centrifugal gel filtration procedure. Antibody integrity was verified by standard biochemical and immunological procedures.

EXAMPLE 17

Preparation of [$^{105}$Rh(BITC-2,3,2-tet)Cl$_2$]$^+$

[$^{105}$Rh(BA-2,3,22,3,2-tet)Cl$_2$]$^+$ was converted to the reactive [$^{105}$Rh(BITC-2,3,2-tet)Cl$_2$]$^+$ derivative ("BITC" refers to p-isothiocyanatobenzyl) by mixing 2 ml of the [$^{105}$Rh(Ba-2,3,22,3,2-tet)Cl$_2$]$^+$ (approximately 5 mCi/ml, 1×10$^{-4}$ M) with 0.002 ml thiophosgene. The reaction was allowed to proceed 15 ; minutes at room temperature. The product was isolated by passing solution through a Hamilton PRP-1 Chrompak. The [$^{105}$Rh(BITC-2,3,2-tet)Cl$_2$]$^+$ eluted with 2 ml of acetonitrile. The product was characterized by comparison to known standards using cation exchange and reverse phase chromatography. Using this procedure yields of between 50 to 85 percent were obtained.

EXAMPLE 17a

Conjugation of [$^{105}$Rh(BITC-2,3,2-tet)Cl$_2$]$^+$ to antibodies

The [$^{105}$Rh(BITC-2,3,2-tet)Cl$_2$]$^+$ was coupled to the lysine residues of tumor specific antibodies (IgG) by the following procedure. The antibodies utilized were CC-49 and B72.3 (the hybridoma cell line B72.3 is deposited at the American Type Culture Collection, 12301 Parklawn Drive, Rockville, Md. and has the accession number ATCC HB 8108), both murine monoclonal antibodies that bind to epitopes of TAG-72, a tumor associated antigen. 1.5×10$^{-5}$ mmole (0.5 mCi) of the [$^{105}$Rh(BITC-2,3,2-tet)Cl$_2$]$^+$ was evaporated to dryness under nitrogen in a 1.5 ml Eppendorff bullet tube. To this dried vessel, 0.10 ml of the appropriate antibody (10 mg/ml in 0.1 M Na$_2$CO$_3$ pH 9.5) was added. The coupling was allowed to proceed 1 hour at room temperature. The $^{105}$Rh labeled antibodies were isolated by centrifugal gel filtration. The antibody integrity was verified by standard biochemical immunological procedures.

EXAMPLE 17b

In Vivo Localization of $^{105}$Rh Labeled Antibodies

The usefulness of the $^{105}$Rh labeled antibodies was demonstrated by measuring the uptake of the materials by a human tumor xenograft in an athymic mouse. Female mice (Nu/Nu) were inoculated subcutaneously (S.C.) (0.1 ml/source) with the human colon carcinoma cell line, LS-174T (approximately 4×10$^6$ cells/animal). Approximately two weeks after inoculation, each animal was injected via the tail vein with 3 uCi (15 $\mu$g) of $^{105}$Rh labeled antibody (CC-49 or B72.3). The mice were sacrificed at various times, the tumor and selected tissues were excised and weighed, and the radioactivity was measured in a gamma counter. The counts per minute per gram of $^{105}$Rh in each tissue (cpm/g) was determined and expressed as a function of the amount injected. The results are shown in the following tables.

Biodistribution of $^{105}$Rh(BITC-2,3,2-tet)Cl$_2$CC-49 IgG in nude mice bearing LS-174T tumors

| Organ | 105Rh | | |
|---|---|---|---|
| | 17 hrs | 40 hrs | 66 hrs |
| Blood | 10.79 ± 0.99 | 8.62 ± 2.46 | 10.46 ± 1.65 |
| Heart | 2.51 ± 0.30 | 2.16 ± 0.45 | 1.96 ± 0.53 |
| Lung | 4.51 ± 0.99 | 4.30 ± 1.14 | 3.91 ± 0.95 |
| Liver | 10.52 ± 3.28 | 10.15 ± 1.50 | 8.22 ± 1.30 |
| Spleen | 5.40 ± 1.14 | 6.93 ± 1.05 | 5.14 ± 0.73 |
| Kidney | 3.43 ± 0.52 | 2.97 ± 0.36 | 2.70 ± 0.73 |
| Muscle | 1.92 ± 0.23 | 1.14 ± 0.30 | 1.15 ± 0.29 |
| Tumor | 35.94 ± 5.38 | 62.03 ± 18.6 | 85.89 ± 23.15 |

Biodistribution of $^{105}$Rh(BITC-2,3,2-tet)Cl$_2$–B72.3 IgG in nude mice bearing Ls-174T tumors

| Organ | 105Rh | | | |
|---|---|---|---|---|
| | 5.5 hrs | 24 hrs | 48 hrs | 72 hrs |
| Blood | 23.44 ± 1.63 | 18.12 ± 1.14 | 13.46 ± 0.57 | 13.07 ± 1.55 |
| Heart | 3.98 ± 0.37 | 3.30 ± 0.19 | 2.70 ± 0.46 | 2.90 ± 1.34 |
| Lung | 7.11 ± 0.91 | 5.96 ± 0.73 | 4.95 ± 0.26 | 4.65 ± 0.76 |
| Liver | 6.08 ± 0.85 | 4.81 ± 0.51 | 3.86 ± 0.26 | 3.77 ± 0.25 |
| Spleen | 4.60 ± 0.64 | 3.95 ± 0.33 | 3.27 ± 0.32 | 3.38 ± 0.54 |
| Kidney | 3.00 ± 0.24 | 3.18 ± 0.29 | 2.35 ± 0.36 | 2.20 ± 0.52 |
| Muscle | 1.21 ± 0.24 | 1.53 ± 0.06 | 1.77 ± 0.41 | 1.52 ± 0.50 |
| Tumor | 13.74 ± 2.02 | 28.07 ± 1.90 | 28.46 ± 4.28 | 34.70 ± 10.78 |

EXAMPLE 18

Conjugation of [$^{105}$Rh(BITC-2,3,2-tet)Cl$_2$]$^+$ to antibody fragments

The [$^{105}$Rh(BITC-2,3,2-tet)Cl$_2$]$^+$ was coupled to the lysine residues of the F(ab')$_2$ fragment of CC-49 antibody by the following procedure. 1.5×10$^{-5}$ mmole (0.5 mCi) of the [$^{105}$Rh(BITC-2,3,2-tet)Cl$_2$]$^+$ was evaporated to dryness under N$_2$ in a 1.5 ml Eppendorf bullet tube. To this dried vessel, 0.10 ml of CC-49 F(ab')2 fragments (10 mg/ml in 0.1 M Na2CO3, pH 9.5) prepared by the enzymatic digestion method described by Lamoyi and Nisonoff (E. Lamoyi and A. Nisonoff, *J. immunol. Methods*, 56, pp. 235–243, (1983)) was added. The reaction was allowed to proceed 1 hour at room temperature. The $^{105}$Rh labeled antibody fragments were isolated by centrifugal gel filtration. The antibody integrity was verified by standard biochemical immunological procedures.

EXAMPLE 19

In Vivo Localization of $^{105}$Rh Labeled CC-49 (Fab')2

The usefulness of the $^{105}$Rh labeled antibody fragments was demonstrated by measuring the uptake of the material by a human tumor xenograft in an athymic mouse. Female athymic mice (Nu/Nu) were inoculated subcutaneously (S.C.) (0.1 ml/source) with the human colon carcinoma cell line, LS-174T (approximately $4 \times 10^6$ cells/animal). Approximately two weeks after inoculation, each animal was injected via the tail vein with 3 μCi (15 μg) of $^{105}$Rh labeled CC-49 (Fab')2 in phosphate buffered saline. The mice were sacrificed at varying times, the tumor and selected tissues were excised and weighed, and radioactivity was measured in a gamma counter. The counts per minute per gram of $^{105}$Rh in each tissue (cpm/g) was determined and expressed as a function of the amount injected. The results are shown in the following table.

Biodistribution of $^{105}$Rh(BITC-2,3,2tet)Cl2-CC-49 F(ab')2 in nude mice bearing LS-174T tumors

| Organ | 24 hrs | $^{105}$Rh 48 hrs | 72 hrs |
|---|---|---|---|
| Blood | 1.32 ± 0.21 | 0.23 ± 0.09 | 0.07 ± 0.01 |
| Heart | 2.53 ± 0.36 | 1.04 ± 0.12 | 1.00 ± 0.15 |
| Lung | 1.64 ± 0.08 | 0.93 ± 0.09 | 0.79 ± 0.42 |
| Liver | 5.43 ± 0.65 | 3.53 ± 0.76 | 2.00 ± 0.43 |
| Spleen | 2.79 ± 0.41 | 2.03 ± 0.29 | 1.00 ± 0.23 |
| Kidney | 37.23 ± 3.27 | 17.19 ± 2.09 | 8.12 ± 1.85 |
| Muscle | 0.94 ± 0.23 | 0.67 ± 0.14 | 0.45 ± 0.10 |
| Tumor | 26.45 ± 4.53 | 22.82 ± 3.00 | 12.76 ± 2.04 |

The biodistribution data presented clearly demonstrates the usefulness of the rhodium chelate/antibody conjugates in localizing on the tumor tissue. The rhodium chelate/antibody conjugates rapidly find the tumor tissue and the remainder clear from the body through the kidneys. Tumor to normal tissue ratios are high indicating that immunodetection and/or therapy is possible.

EXAMPLE 20

In a similar manner to that described in Example 19, athymic mice bearing LS-174T tumors were injected with rhodium chelate/antibody conjugates, ($^{105}$Rh labelled, both antibody fragments (i.e., (F(ab')2) and whole IgG monoclonal antibodies were respectively tested. At various times after injection, gamma ray images of the entire animal were obtained using the 319 and 306 kev gamma rays. The images showed rapid clearance of the radioactivity from the blood and uptake in the tumor in agreement with the quantitative results obtained in Example 19.

In using the rhodium chelate/antibody conjugates of the present invention for the diagnosis or treatment of a disease state in a mammal, the rhodium chelate/antibody conjugates are preferably administered in the form of a composition comprising the rhodium chelate/antibody conjugate in admixture with a pharmaceutically acceptable carrier (i.e., a carrier which is inert to the active material and which has no significant detrimental side effects or toxicity under conditions of use). The rhodium chelate/antibody composition is administered in a manner suitable for the particular application, typically parenterally, for example, by intraperitoneal, subcutaneous or intravenous injection. In such applications, an effective amount (i.e., an amount sufficient to provide the desired effect) of one or more of the rhodium chelate/antibody conjugates is employed in the composition. Selection of the particular rhodium chelate/antibody conjugate or conjugates to be employed in the composition. Selection of the particular rhodium chelate/antibody conjugate or conjugates to be employed in a particular composition is dictated by considerations such as ease of administration, stability, compatibility with suitable carriers, etc. In particular cases, the amount to be administered can be ascertained by procedures well known in the art. The compositions which are administered are typically in liquid form such as sterile injectable suspensions or solutions. Pharmaceutically acceptable carriers to be employed in any particular situation can be readily determined and are well known in the art and may, in addition, optionally contain other active materials and/or excipients.

We claim:

1. A rhodium complex which comprises rhodium, in which at least a portion of the rhodium is radioactive rhodium, complexed with a compound of the formula:

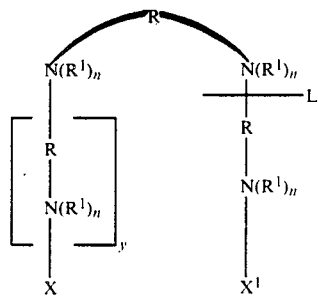

wherein:
- each R independently represents a straight-chained or branched alkylene group of 2 to 10 carbon atoms inclusive, with the proviso that for any two adjacent nitrogens connected by an R group the R group must provide at least three single bonds between the nitrogens it connects;
- each $R^1$ independently represents hydrogen or a straight-chained or branched alkylene group of 1 to 10 carbon atoms inclusive;
- X an $X^1$ represent H, or X and $X^1$ taken together complete a bridging straight-chained or branched alkylene group of 2 to 10 carbon atoms inclusive or a bridging aralkylene group wherein the alkylene is a straight-chained or branched alkylene group of 2 to 10 carbon atoms inclusive, with the proviso that when X and $X^1$ are taken together the group it represents must provide at least three single bonds between the adjacent nitrogens it connects;
- n is an integer of 0 or 1, provided that when the : group is bonded to the same nitrogen atom, n must be 0, otherwise n must be 1;

y is an integer of 1 through 3 inclusive; and

L is a linker/spacer group covalently bonded to, and replaces one hydrogen atom of, any one of the nitrogen or carbon atoms, said linker/spacer group being represented by the formula

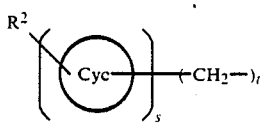

wherein:

s represents an integer of 1;

t represents an integer of 0 through 20 inclusive;

$R^2$ represents an electrophilic or nucleophilic moiety which allows for covalent attachment to an antibody or nucleophilic moiety which allows for covalent attachment to an antibody or fragment thereof, or a synthetic linker which can be attached to an antibody or fragment thereof; and Cyc represents an aromatic moiety, aliphatic heterocyclic moiety, or aromatic heterocyclic moiety, each of said moieties optionally substituted with one or more groups which do not interfere with binding to an antibody or antibody fragment.

2. The rhodium complex of claim 1 wherein at least a portion of the rhodium is $^{105}$Rh.

3. A rhodium complex which comprises rhodium, in which at least a portion of the rhodium is radioactive rhodium, complexed with the compound set forth in claim 1 wherein R is an alkylene group having 2 or 3 carbon atoms; $R^1$ is a hydrogen or methyl; X and $X^1$ represent hydrogen, or X and $X^1$ taken together represent an alkylene group having 2 or 3 carbon atoms.

4. The rhodium complex of claim 3 wherein at least a portion of the rhodium is $^{105}$Rh.

5. A rhodium complex of the formula $[RhChP_1P_2]A$ wherein:

Rh represents a rhodium atom, wherein at least a portion of the rhodium is $^{105}$Rh;

Ch represents the compound set forth in claim 1 that is complexed;

$P_1$ and $P_2$ each represent the same or different monodentate ligand, or $P_1$ and $P_2$ taken together represent a bidentate ligand, provided, however, that (a) if y is 2 then $P_2$ is absent, or (b) if y is 3 then $P_1$ and $P_2$ are absent; and A represents one or more anions of sufficient charge to render the rhodium complex neutral.

6. A rhodium complex of claim 5 103 wherein the compound is selected from 3-[4-(aminophenyl)methyl -1,5,8,12-tetraazacyclotetradecane, 6-[4-(aminophenyl)- methyl]1,4,8,11-tetraazaundecane, and 1,4,7,10-tetraaza1-[(4-aminophenyl)methyl[cyclododecane.

7. A rhodium complex which comprises rhodium, in which at least a portion of the rhodium is radioactive rhodium, complexed with the compound set forth in claim 1 wherein L is

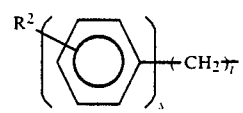

wherein:

$R^2$, s and t are defined as in claim 1.

8. The rhodium complex of claim 7 wherein at least a portion of the rhodium is $^{105}$Rh.

9. A rhodium complex which comprises rhodium, in which at least a portion of the rhodium is radioactive rhodium, complexed with the compound set forth in claim 7 wherein R is an alkylene group having 2 or 3 carbon atoms; $R^1$ is hydrogen or methyl; X and $X^1$ represent hydrogen, or X and $X^1$ taken together represent an alkylene group having 2 or 3 carbon atoms.

10. The rhodium complex of claim 9 wherein at least a portion of the rhodium is $^{105}$Rh.

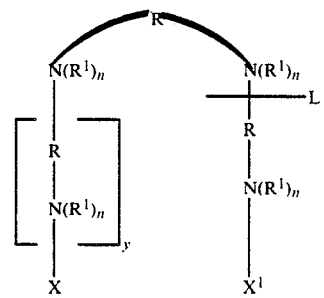

11. A rhodium complex which comprises rhodium, in which at least a portion of the rhodium is radioactive rhodium, complexed with the compound set forth in claim 9 wherein t is an integer of 0 through 6 inclusive; and y is the integer 1.

12. The rhodium complex of claim 11 wherein at least a portion of the rhodium is $^{105}$Rh.

wherein:

each R independently represents a straight-chained or branched alkylene group of 2 or 3 carbon atoms inclusive, with the proviso that for any two adjacent nitrogens connected by an R group the R group must provide at least three single bonds between the nitrogens it connects;

each $R^1$ independently represents hydrogen or methyl;

X and $X^1$ represent H, or X and $X^1$ taken together complete a bridging straight-chained or branched alkylene group of 2 or 3 carbon atoms inclusive, with the proviso that when X and $X^1$ are taken together the group it represents must provide at least three single bonds between the adjacent nitrogens it connects;

n is an integer of 0 or 1, provided that when the L group is bonded to the same nitrogen atom, n must be 0, otherwise n must be 1;

y is an integer of 1; and

L is a linker/spacer group covalently bonded to, and replaces one hydrogen atom of, any one of the nitrogen or carbon atoms, said linker/spacer group being represented by the formula

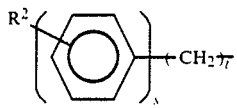

wherein:

s represents an integer of 1;

t represents an integer of 0 through 6 inclusive;

$R^2$ represents isothiocyanato, semicarbazido, thiosemicarbazido, amino or carboxyl.

13. A rhodium complex which comprises rhodium, in which at least a portion of the rhodium is radioactive rhodium, complexed with a compound of the formula:

14. The rhodium complex of claim 13 wherein at least a portion of the rhodium is $^{105}$Rh.

15. A rhodium complex of claim 13 which comprises rhodium, in which at least a portion of the rhodium is radioactive rhodium, complexed with a compound selected from 3-[4-(aminophenyl)methyl]-1,5,8,12-tetraaza-cyclotetradecane, 6-[4-(aminophenyl)methyl]-1,4,8,11-tetraazaundecane, and 1,4,7,10-tetraaza-1-[(4-aminophenyl)methyl]cyclododecane.

16. The rhodium complex of claim 15 wherein at least a portion of the rhodium is $^{105}$Rh.

* * * * *